US009889230B2

(12) United States Patent
Bennett et al.

(10) Patent No.: US 9,889,230 B2
(45) Date of Patent: *Feb. 13, 2018

(54) HEMOSTATIC IMPLANT

(75) Inventors: Steven Bennett, Cheshire, CT (US); Timothy Sargeant, Guilford, CT (US)

(73) Assignee: Covidien LP, Mansfield, MA (US)

( * ) Notice: Subject to any disclaimer, the term of this patent is extended or adjusted under 35 U.S.C. 154(b) by 928 days.

This patent is subject to a terminal disclaimer.

(21) Appl. No.: 12/938,491

(22) Filed: Nov. 3, 2010

(65) Prior Publication Data
US 2011/0045047 A1    Feb. 24, 2011

Related U.S. Application Data

(63) Continuation-in-part of application No. 12/573,176, filed on Oct. 5, 2009.

(60) Provisional application No. 61/196,543, filed on Oct. 17, 2008.

(51) Int. Cl.
| *A61L 27/52* | (2006.01) |
| *A61L 27/24* | (2006.01) |
| *A61L 27/34* | (2006.01) |
| *A61L 27/48* | (2006.01) |
| *A61L 27/56* | (2006.01) |

(52) U.S. Cl.
CPC ............. *A61L 27/52* (2013.01); *A61L 27/24* (2013.01); *A61L 27/34* (2013.01); *A61L 27/48* (2013.01); *A61L 27/56* (2013.01); *A61L 2400/04* (2013.01); *A61L 2420/08* (2013.01); *A61L 2430/06* (2013.01)

(58) Field of Classification Search
None
See application file for complete search history.

(56) References Cited

U.S. PATENT DOCUMENTS

| 3,364,200 A | 10/1968 | Ashton et al. |
| 3,666,750 A | 5/1972 | Briskin et al. |
| 3,937,223 A | 2/1976 | Roth |
| 4,511,478 A | 4/1985 | Nowinski et al. |
| 4,626,253 A | 12/1986 | Broadnax, Jr. |
| 4,663,163 A | 5/1987 | Hou et al. |
| 4,826,945 A | 5/1989 | Cohn et al. |
| 4,938,763 A | 7/1990 | Dunn et al. |
| 5,100,992 A | 3/1992 | Cohn et al. |
| 5,160,745 A | 11/1992 | DeLuca et al. |
| 5,201,745 A | 4/1993 | Tayot et al. |
| 5,410,016 A | 4/1995 | Hubbell et al. |
| 5,484,913 A | 1/1996 | Stilwell et al. |
| 5,505,952 A | 4/1996 | Jiang et al. |
| 5,514,379 A | 5/1996 | Weissleder et al. |
| 5,527,864 A | 6/1996 | Suggs et al. |
| 5,580,923 A | 12/1996 | Yeung et al. |
| 5,626,863 A | 5/1997 | Hubbell et al. |
| 5,643,596 A | 7/1997 | Pruss et al. |
| 5,645,849 A | 7/1997 | Pruss et al. |
| 5,752,974 A | 5/1998 | Rhee et al. |
| 6,152,943 A | 11/2000 | Sawhney |
| 6,162,241 A | 12/2000 | Coury et al. |
| 6,165,201 A | 12/2000 | Sawhney et al. |
| 6,179,862 B1 | 1/2001 | Sawhney |
| 6,376,742 B1 | 4/2002 | Zdrahala et al. |
| 6,500,777 B1 | 12/2002 | Wiseman et al. |
| 6,514,534 B1 | 2/2003 | Sawhney |
| 6,566,406 B1 | 5/2003 | Pathak et al. |
| 6,605,294 B2 | 8/2003 | Sawhney |
| 6,673,093 B1 | 1/2004 | Sawhney |
| 6,703,047 B2 * | 3/2004 | Sawhney ............. A61K 9/0075 424/422 |
| 6,800,753 B2 | 10/2004 | Kumar |
| 6,818,018 B1 | 11/2004 | Sawhney |
| 6,833,408 B2 | 12/2004 | Sehl et al. |
| 6,936,005 B2 | 8/2005 | Poff et al. |
| 6,969,400 B2 | 11/2005 | Rhee et al. |
| 7,009,034 B2 | 3/2006 | Pathak et al. |
| 7,052,713 B2 | 5/2006 | Stimmeder |
| 7,176,256 B2 | 2/2007 | Rhee et al. |
| 7,347,850 B2 | 3/2008 | Sawhney |
| 2002/0106409 A1 | 8/2002 | Sawhney et al. |
| 2003/0031697 A1 | 2/2003 | Chudzik et al. |
| 2003/0035786 A1 | 2/2003 | Hendriks et al. |
| 2003/0073663 A1 | 4/2003 | Wiseman et al. |
| 2004/0001879 A1 | 1/2004 | Guo et al. |
| 2004/0023842 A1 | 2/2004 | Pathak et al. |

(Continued)

FOREIGN PATENT DOCUMENTS

| EP | 0627911 | 10/2000 |
| EP | 2 143 737 A1 | 1/2010 |

(Continued)

OTHER PUBLICATIONS

Davis et al. (Sugar crosslinked gelatin for controlled release: microspheres and disks, Biomaterials, 1998, vol. 19, pp. 1641-1649).*
International Search Report issued in Application EP 11250562.3 mailed Dec. 8, 2011.
International Search Report issued in Application EP 11250564.9 mailed Dec. 8, 2011.
International Search Report issued in Application EP 11250563.1 mailed Dec. 27, 2011.
International Search Report issued in Application EP 11250566.4 mailed Dec. 22, 2011.
International Search Report issued in Application EP 11250565.6 mailed Dec. 23, 2011.

(Continued)

*Primary Examiner* — Kevin S Orwig
*Assistant Examiner* — Ping Cao

(57) ABSTRACT

The present disclosure relates to collagen-containing implants including a porous substrate having a first hydrogel precursor and a second hydrogel precursor applied thereto in a manner such that the first hydrogel precursor and second hydrogel precursor do not react with each other until the implant is placed at the site of implantation and exposed to the physiological fluids of a patient.

24 Claims, 13 Drawing Sheets

(56) References Cited

U.S. PATENT DOCUMENTS

| | | |
|---|---|---|
| 2004/0101546 A1 | 5/2004 | Gorman et al. |
| 2004/0106344 A1 | 6/2004 | Looney et al. |
| 2004/0191277 A1 | 9/2004 | Sawhney et al. |
| 2004/0265371 A1 | 12/2004 | Looney et al. |
| 2005/0175665 A1* | 8/2005 | Hunter et al. ............... 424/423 |
| 2006/0034930 A1 | 2/2006 | Khosravi et al. |
| 2006/0099238 A1* | 5/2006 | Khosravi et al. ............ 424/423 |
| 2006/0159733 A1 | 7/2006 | Pendharkar et al. |
| 2006/0233869 A1 | 10/2006 | Looney et al. |
| 2007/0014862 A1 | 1/2007 | Pameijer et al. |
| 2007/0123817 A1 | 5/2007 | Khosravi et al. |
| 2007/0190110 A1 | 8/2007 | Pameijer et al. |
| 2007/0275073 A1 | 11/2007 | Huey et al. |
| 2008/0027365 A1 | 1/2008 | Huey |
| 2008/0114092 A1 | 5/2008 | Sawhney |
| 2008/0139694 A1 | 6/2008 | Ratcliffe |
| 2008/0160051 A1 | 7/2008 | Sirota |
| 2008/0194805 A1 | 8/2008 | Vignon et al. |
| 2008/0241203 A1* | 10/2008 | Morinaga ............ A61L 31/148 424/402 |
| 2009/0117070 A1 | 5/2009 | Daniloff et al. |
| 2010/0100123 A1* | 4/2010 | Bennett ........................ 606/213 |
| 2011/0070288 A1 | 3/2011 | Andjelic |
| 2011/0081397 A1* | 4/2011 | Skalla et al. ................. 424/423 |

FOREIGN PATENT DOCUMENTS

| | | | |
|---|---|---|---|
| EP | 2 196 193 A1 | 6/2010 | |
| EP | 2 233 160 A2 | 9/2010 | |
| EP | 2 233 161 A2 | 9/2010 | |
| JP | 2008-521502 A | 6/2008 | |
| JP | 2010-94519 A | 4/2010 | |
| WO | WO 94/03155 | 2/1994 | |
| WO | WO2005094915 | * 10/2005 | ............... A61K 9/00 |
| WO | 2010043980 A2 | 4/2010 | |

OTHER PUBLICATIONS

Japanese Office Action from Appl. No. 2011-241476 mailed Oct. 1, 2015.

Notice of Final Rejection issued in Japanese Appl. No. 2011-241476 mailed May 30, 2016.

Extended European Search Report from Application No. EP 11187581.1.

Extended European Search Report from Appl. No. EP 16197104.9 dated Feb. 16, 2017.

Canadian Office Action issued in Appl. No. CA 2,755,617 dated Nov. 22, 2017.

* cited by examiner

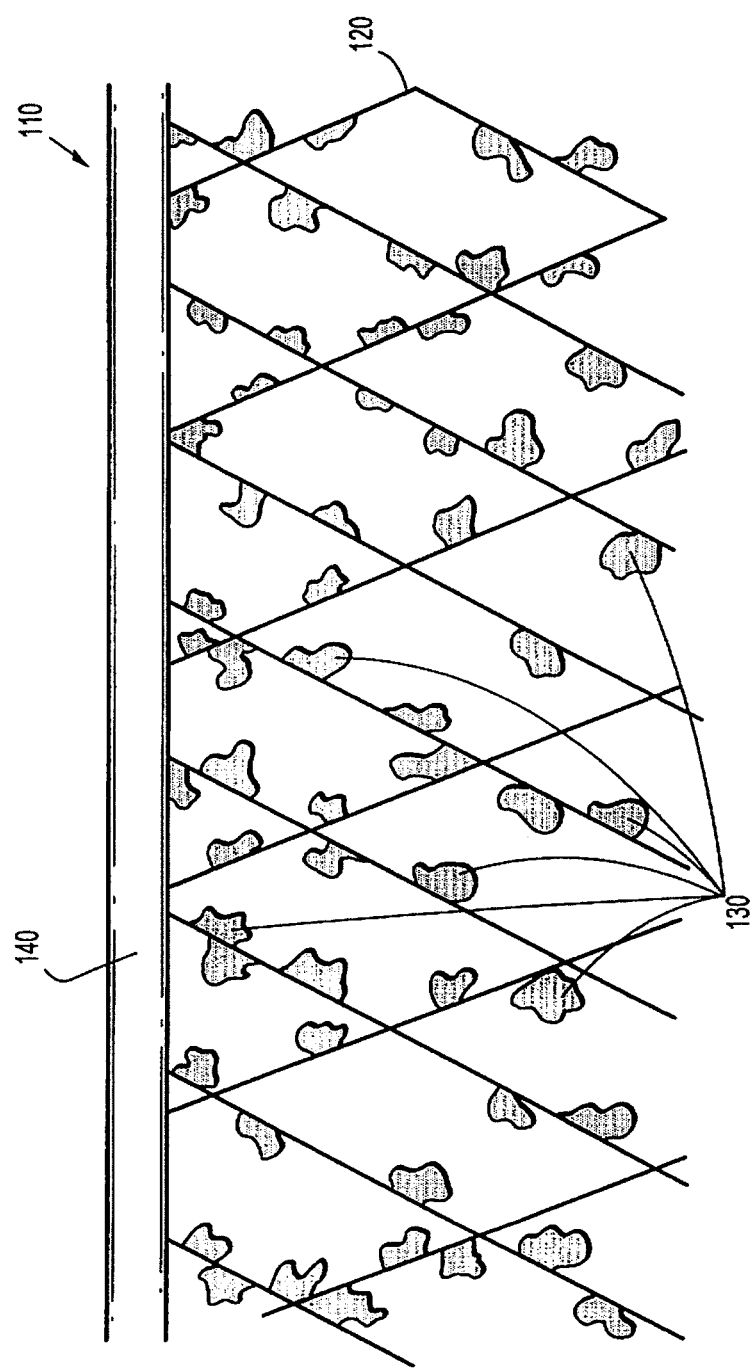

HEMOSTATIC IMPLANT

RELATED APPLICATIONS

This application is a continuation in part of co-pending U.S. patent application Ser. No. 12/573,176, filed on Oct. 5, 2009 which, in turn, claims the benefit of and priority to U.S. Provisional Application No. 61/196,543 filed Oct. 17, 2008.

BACKGROUND

The present disclosure relates to implants and more particularly to collagen-containing implants which include a porous substrate having a first hydrogel precursor and a second hydrogel precursor applied thereto.

In situ cartilage defect therapy has primarily focused on creating a tissue scaffold by transforming precursor solutions into a solid implant within a cartilage defect or mechanically fixating a preformed tissue scaffold to a cartilage defect. Transformations of precursor solutions have been achieved by a variety of means, including precipitation, polymerization, crosslinking, and desolvation. However, significant limitations exist when using solutions for in situ cartilage defect therapy. Solutions of low viscosity may flow away and be cleared from an application site before transformation and solidification occurs. Furthermore, formulation of the solutions may be complex, as preparation of precursor solutions typically requires reconstitution of the precursors, or, when the solutions are stored frozen, thawing. Mechanical fixation of three-dimensional scaffolds typically requires the use of sutures, tacks or other mechanical means of attachment that involve further tissue damage to affix the implant to the tissue adjoining the cartilage defect.

Therefore it would be desirable to provide in situ cartilage defect therapy which includes implantable devices combined with dry materials that are activated by the presence of aqueous physiological fluids. The combination of an implantable device with dry materials ensures the in situ hemostatic therapy will occur at the site of implantation.

SUMMARY

The present disclosure provides implants and methods for using same. In embodiments, the present disclosure provides an implant including a porous substrate having a first hydrogel precursor including collagen applied to the porous substrate, and a film containing a second hydrogel precursor applied to the porous substrate. The porous substrate may be a foam, a knitted textile, a non-woven textile, combinations thereof, and the like. The porous substrate may be made of a bioabsorbable material, and/or a non-bioabsorbable material.

In other embodiments, an implant of the present disclosure may include a porous substrate having a first hydrogel precursor including collagen applied to a first portion of the porous substrate; and a second hydrogel precursor applied to a second portion of the porous substrate, wherein the first portion of the substrate is spatially separated from the second portion of the porous substrate.

Methods of the present disclosure include, in embodiments, identifying a defect in cartilage; orienting a porous substrate having a first hydrogel precursor including collagen applied to a first portion of the porous substrate and a second hydrogel precursor applied to a second portion of the porous substrate, with the second portion nearer to a patient's tissue within the defect than the first portion; and contacting the oriented implant with the patient's tissue, wherein physiological fluids wet the second portion and are wicked through the porous substrate so that the first hydrogel precursor reacts with the second hydrogel precursor, thereby forming a hydrogel.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

FIG. 2 schematically shows a variation of the embodiment shown in FIGS. 1A-1D;

DETAILED DESCRIPTION

Figure 1A:
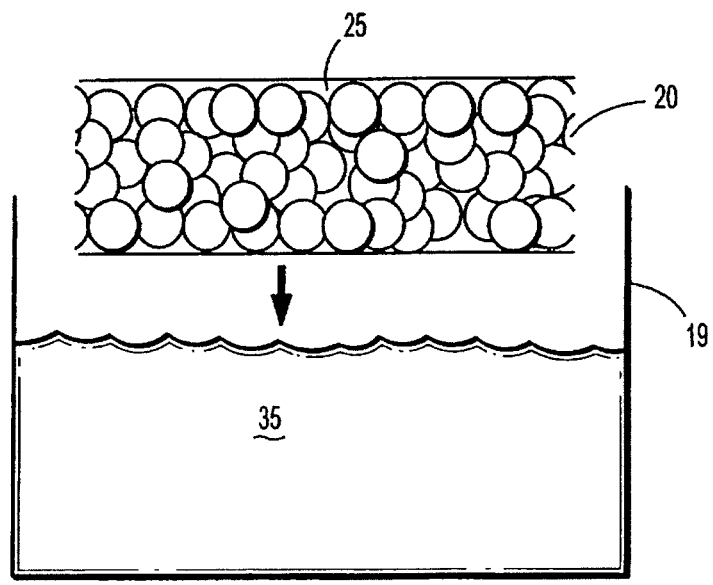
FIGS. 1A-D schematically show the application of first and second hydrogel precursors to a porous substrate as described in at least one of the embodiments in the present disclosure.

Collagen-containing implants in accordance with the present disclosure include a porous substrate having a first hydrogel precursor applied to a first portion of the porous substrate and a second hydrogel precursor applied to a second portion of the porous substrate. During use, the implant is oriented with the portion to which the first hydrogel precursor is applied closer to the tissue and the portion having the second hydrogel precursor applied thereto further from the tissue. In embodiments, the first and second portions may be distinguishable from one another by the addition of contrast dyes, surface texturing, coloring or other visual cues. Upon contact with tissue, such as, for example, injured tissue, the implant will soak up physiological fluid and the first hydrogel precursor will be dissolved by the fluid. As the fluid wicks into and migrates across the implant, it will carry the dissolved first hydrogel precursor along through the implant. Eventually, the fluid will migrate through the implant sufficiently to reach the second portion to which the second hydrogel precursor is applied, thereby dissolving the second hydrogel precursor. The first and second hydrogel precursors will then react to form a biocompatible cross linked material, thereby assisting tissue ingrowth and remodeling as the scaffold degrades. In some embodiments, the biocompatible cross linked material produced by reaction of the first and second hydrogel precursors also provide the implant with anti-adhesive properties.

The porous substrate of the implant has openings or pores over at least a portion of a surface thereof. The pores may be formed in the substrate either before or after implantation. As described in more detail below, suitable materials for forming the porous substrate include, but are not limited to fibrous structures (e.g., knitted structures, woven structures, non-woven structures, etc.) and/or foams (e.g., open or closed cell foams). In embodiments, the pores may be in sufficient number and size so as to interconnect across the entire thickness of the porous substrate. Woven fabrics, kitted fabrics and open cell foam are illustrative examples of structures in which the pores can be in sufficient number and size so as to interconnect across the entire thickness of the porous substrate. In embodiments, the pores do not interconnect across the entire thickness of the porous substrate. Closed cell foam or fused non-woven materials are illustrative examples of structures in which the pores may not interconnect across the entire thickness of the porous substrate. The pores of the foam porous substrate may span across the entire thickness of porous substrate. In yet other embodiments, the pores do not extend across the entire thickness of the porous substrate, but rather are present at a portion of the thickness thereof. In embodiments, the openings or pores are located on a portion of the surface of the porous substrate, with other portions of the porous substrate having a non-porous texture. In other embodiments, the pores may be formed after implantation in situ. The in situ pore formation may be performed using any suitable method. Some non-limiting examples include the use of contact lithography, living radical photopolymer (LRPP) systems and salt leaching. Those skilled in the art reading the present disclosure will envision other pore distribution patterns and configurations for the porous substrate.

Where the porous substrate is fibrous, the fibers may be filaments or threads suitable for knitting or weaving or may be staple fibers, such as those frequently used for preparing non-woven materials. The fibers may be made from any biocompatible material. Thus, the fibers may be formed from a natural material or a synthetic material. The material from which the fibers are formed may be bioabsorbable or non-bioabsorbable. It should of course be understood that any combination of natural, synthetic, bioabsorbable and non-bioabsorbable materials may be used to form the fibers.

Some non-limiting examples of materials from which the fibers may be made include, but are not limited to poly(lactic acid), poly (glycolic acid), poly(lactide, poly(glycolide), poly(trimethylene carbonate), poly (dioxanone), poly (hydroxybutyrate), poly (phosphazine), polyesters, polyethylene terephthalate, ultra-high molecular weight polyethylene, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly (amino acids), copoly (ether-esters), polyalkylene oxalates, poly (saccharides), polyamides, poly (iminocarbonates), polyalkylene oxalates, polyoxaesters, polyorthoesters, polyphosphazenes, biopolymers, polymer drugs and copolymers, block copolymers, homopolymers, blends and combinations thereof.

Where the porous substrate is fibrous, the porous substrate may be formed using any method suitable to forming fibrous structures, including but not limited to knitting, weaving, non-woven techniques, wet-spinning, electro-spinning, extrusion, co-extrusion, and the like. Suitable techniques for making fibrous structures are within the purview of those skilled in the art. In embodiments, the textile has a three dimensional structure, such as the textiles described in U.S. Pat. Nos. 7,021,086 and 6,443,964, the disclosures of which are incorporated herein by this reference in their entirety.

In embodiments, the porous substrate is made from fibers of oxidized cellulose. Such materials are known and include oxidized cellulose hemostat materials commercially available under the trade name SURGICEL®. Methods for preparing oxidized cellulose hemostat materials are known to those skilled in the art and are disclosed, for example in U.S. Pat. Nos. 3,364,200; 4,626,253; 5,484,913; and 6,500,777, the disclosures of which are incorporated herein by this reference in their entirety.

Where the porous substrate is a foam, the porous substrate may be formed using any method suitable to forming a foam or sponge including, but not limited to the lyophilization or freeze-drying of a composition. The foam may be cross-linked or non-cross-linked, and may include covalent or ionic bonds. Suitable techniques for making foams are within the purview of those skilled in the art.

The porous substrate can be at least 0.1 cm thick, in embodiments from about 0.2 to about 1.5 cm thick. The size of the pores in the porous substrate can be from about 2 μm to about 300 μm, in embodiments from about 50 μm to about 150 μm. It is envisioned that the pores of the substrate may be arranged in any manner in the substrate. For example, the pores may be configured in a random or uniform manner. In some embodiments, the pores may be formed with the use of copper alginate to create a honey-comb shaped porous substrate. In still other embodiments, the pores may be configured to create a gradient in the porous substrate. The gradient may further enhance the porous substrates ability to absorb the physiologic fluid and direct the migration of the physiological fluid carrying the first hydrogel precursor towards the second hydrogel precursor.

In embodiments, the implant is a made from non-denatured collagen or collagen which has at least partially lost its helical structure through heating or any other method, consisting mainly of non-hydrolyzed α chains, of molecular weight close to 100 kDa. The term "non-denatured collagen" means collagen which has not lost its helical structure. The collagen used for the implant of present invention may be native collagen or atelocollagen, notably as obtained through pepsin digestion and/or after moderate heating as defined previously. The collagen may have been previously chemically modified by oxidation, methylation, ethylation, succinylation or any other known process. The collagen may also be cross-linked with any suitable crosslinker, such as genipin, isocyanates, and aldehydes. The origin and type of collagen may be as indicated for the non-implant described above.

In other embodiments, collagen, including any collagen described herein, may be utilized as one of the precursors. As described in greater detail below, amine groups on a collagen precursor, which are nucleophilic, may be free to react with electrophilic groups on a second precursor, thereby forming a hydrogel of the present disclosure.

In embodiments, the implant can be obtained by freeze-drying an aqueous acid solution of collagen at a concentration of 2 to 50 grams/liter (g/l) and an initial temperature of 4 to 25° C. The concentration of collagen in the solution can be from about 1 g/l to about 30 g/l, in embodiments about 10 g/l. This solution is advantageously neutralized to a pH of around 6 to 8.

The implant can also be obtained by freeze-drying a fluid foam prepared from a solution of collagen or heated collagen, emulsified in the presence of a volume of air in variable respective quantities (volume of air:water varying from about 1 to about 10).

The porous substrate has a first hydrogel precursor applied thereto and a second hydrogel precursor applied thereto. The terms "first hydrogel precursor" and "second hydrogel precursor" each means a polymer, functional polymer, macromolecule, small molecule, or crosslinker that can take part in a reaction to form a network of crosslinked molecules, e.g., a hydrogel.

Each of the first and second hydrogel precursors is multifunctional, meaning that it comprises two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form crosslinked polymeric products. Such reactions are referred to as "crosslinking reactions".

In embodiments, each of the first and second hydrogel precursors includes only one category of functional groups, either only nucleophilic groups or only electrophilic functional groups, so long as both nucleophilic and electrophilic precursors are used in the crosslinking reaction. Thus, for example, if the first hydrogel precursor has nucleophilic functional groups such as amines, the second hydrogel precursor may have electrophilic functional groups such as N-hydroxysuccinimides. On the other hand, if first hydrogel precursor has electrophilic functional groups such as sulfosuccinimides, then the second hydrogel precursor may have nucleophilic functional groups such as amines or thiols. Thus, functional polymers such as proteins, poly(allyl amine), styrene sulfonic acid, or amine-terminated di- or multifunctional poly(ethylene glycol) ("PEG") can be used.

The first and second hydrogel precursors may have biologically inert and water soluble cores. When the core is a polymeric region that is water soluble, preferred polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, hydroxynethylcellulose, hyaluronic acid; and proteins such as albumin, collagen, casein, and gelatin. The polyethers and more particularly poly(oxyalkylenes) or poly(ethylene glycol) or polyethylene glycol are especially useful. When the core is small molecular in nature, any of a variety of hydrophilic functionalities can be used to make the first and second hydrogel precursors water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

In embodiments, both the first and second hydrogel precursors may be large molecules that are capable of crosslinking. For example, in embodiments, one of the precursors may be a multi-functional PEG having a molecular weight of from about 2,000 to about 20,000 Daltons. This multifunctional PEG, in embodiments possessing electrophilic groups, may be reacted with a collagen having a molecular weight of about 100,000 Daltons. In other embodiments, a gelatin having a molecular weight of from about 50,000 to about 100,000 Daltons may be used in place of the collagen. Utilizing these large molecule precursors, the resulting hydrogels may be used as tissue scaffolds suitable for applications including cartilage repair.

If it is desired that the biocompatible crosslinked polymer resulting from the reaction of the first and second hydrogel precursors be biodegradable or absorbable, one or more of the first and second hydrogel precursors may have biodegradable linkages present between the functional groups. The biodegradable linkage optionally also may serve as the water soluble core of one or more of the precursors. In the alternative, or in addition, the functional groups of the first and second hydrogel precursors may be chosen such that the product of the reaction between them results in a biodegradable linkage. For each approach, biodegradable linkages may be chosen such that the resulting biodegradable biocompatible crosslinked polymer will degrade, dissolve or be absorbed in a desired period of time. Preferably, biodegradable linkages are selected that degrade under physiological conditions into non-toxic products.

The biodegradable linkage may be chelates or chemically or enzymatically hydrolyzable or absorbable. Illustrative chemically hydrolyzable biodegradable linkages include polymers, copolymers and oligomers of glycolide, dl-lactide, 1-lactide, caprolactone, dioxanone, and tritnethylene carbonate. Illustrative enzymatically hydrolyzable biodegradable linkages include peptidic linkages cleavable by metalloproteinases and collagenases. Additional illustrative biodegradable linkages include polymers and copolymers of poly(hydroxy acid)s, poly(orthocarbonate)s, poly (anhydride)s, poly(lactone)s, poly(amino acid)s, poly(carbonate)s, poly(saccharide)s and poly(phosphonate)s.

In embodiments, the biodegradable linkage may contain ester linkages. Some non-limiting examples include esters of succinic acid, glutaric acid, propionic acid, adipic acid, or amino acids, as well as carboxymethyl esters.

In embodiments, a multifunctional electrophilic polymer such as a multi-arm PEG functionalized with multiple NHS groups may be used as a first hydrogel precursor, and a multifunctional nucleophilic component such as trilysine may be used as a second hydrogel precursor. In other embodiments, a multifunctional electrophilic polymer such as a multi-aim PEG functionalized with multiple NHS groups may be used as a first hydrogel precursor, and a multifunctional nucleophilic polymer such as collagen and/or a collagen derivative may be used as a second hydrogel precursor. The multi-arm PEG functionalized with multiple NHS groups can for example have four, six or eight arms and have a molecular weight of from about 5,000 to about 25,000. Many other examples of suitable first and second precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire content of each of which is incorporated herein by reference.

The first hydrogel precursor is applied to a first portion of the porous substrate and a second hydrogel precursor applied to a second portion of the porous substrate. For example, the precursors may be applied in a dry form, such as particulate matter or in a solid or semi-solid state such as a film, or foam. In embodiments, at least one of the first or second hydrogel precursors is applied to the porous substrate as a film. In embodiments, the first portion of the substrate having the first hydrogel precursor applied thereto is spatially separated from the second portion of the porous substrate having the second hydrogel precursor applied thereto. Having the first and second hydrogel precursors spatially separated from each other prevents them from reacting with each other until the implant is placed at the site of implantation and exposed to the physiological fluids of a patient.

The first hydrogel precursor may be applied to the porous substrate using any suitable method known to those skilled in the art, including, but not limited to spraying, brushing, dipping, pouring, laminating, etc. In embodiments, the first hydrogel precursor may be applied as a coating on the substrate in any concentration, dimension and configuration capable of forming a hemostatic implant. In embodiments, the first hydrogel precursor coating may penetrate the pores of the porous substrate. The coating may form a non-porous layer or a porous layer. In embodiments, the first hydrogel precursor may be applied to the porous substrate as a film that is laminated onto at least one side of the substrate.

The second hydrogel precursor likewise may be applied to the porous substrate using any suitable method known to those skilled in the art, including, but not limited to spraying, brushing, dipping, pouring, laminating, etc. In embodiments, the second hydrogel precursor may be incorporated into the porous substrate prior to forming the porous substrate. In other embodiments, the second hydrogel precursor may be positioned in the pores of the porous substrate or onto a surface of the porous substrate following formation of the substrate. In yet other embodiments, the porous substrate may be calendered prior to application of the second hydrogel precursor thereby allowing the second precursor to penetrate into openings on the substrate which were created by the calendering process. In still other embodiments, the second hydrogel precursor may be applied to the porous substrate in solution followed by evaporation or lyophilization of the solvent. In embodiments, the second hydrogel precursor may be applied to the porous substrate as a coating on at least one side of the substrate or as a film laminated onto at least one side of the substrate.

In embodiments where either the first or second hydrogel precursor forms a non-porous layer, i.e., a film, the thickness of the film may be sufficient to allow for only portions of the hydrogel precursor to react with the other hydrogel precursor before the implant seals a wound. In such embodiments, the remaining unreacted hydrogel film may act as a barrier layer between the wound and the surrounding tissue to prevent the formation of adhesions. In forming the hydrogel implant, the precursors may also impart upon the physiological fluids certain properties, such as anti-adhesion. The physiological fluid-/hydrogel may also act as a barrier layer between the wound and the surrounding tissue to prevent the formation of adhesions. In embodiments, the porous substrate may further contain non-reactive materials that are known to reduce or prevent adhesions, such as hyaluronic acid and the like. In such embodiments, the non-reactive materials may prevent the formation of adhesions after the first and second hydrogel precursors interact.

In other embodiments, implants of the present disclosure may be utilized as a three-dimensional biodegradable scaffold. The three-dimensional scaffold may facilitate tissue ingrowth and remodeling as the scaffold degrades. In embodiments, the scaffold is self-adhesive. The implant may thus be applied to tissue and fixed in place without the need for glues, sutures, staples, tacks, or other methods of secondary adhesion. Tissue scaffolds of the present disclosure may be used to repair various defects, including cartilage defects; neural repair (brain, spinal cord, etc.), organ defects such as heart (myocardial infarction), kidney, and liver; muscle, fat (breast augmentation, body contouring, facial implants, etc.), tendon/ligament repair, bones, and the like.

For example, in embodiments, a cellulose scaffold may be constructed which is about the same thickness of human cartilage found in the knee, i.e., about 3 mm. The cellulose may be impregnated with collagen and basic salts. Suitable basic salts include metal salts of borates, including sodium borate and potassium borate; carbonates, including sodium carbonate and potassium carbonate; phosphates, including mono and dibasic sodium phosphate and potassium phosphate; bicarbonates, including sodium bicarbonate and potassium bicarbonate; combinations of the foregoing, and the like. In embodiments, the collagen may be dissolved in a basic buffer, for example a borate buffer having a pH of about 8.75. The cellulose may then be soaked in the buffer and immediately freeze dried. A multi-armed electrophilic PEG as described above may then be applied as a layer to the cellulose scaffold and dried to form an implant of the present disclosure. In other embodiments, the PEG layer may be dry coated onto one side of the cellulose.

For use in cartilage repair, the resulting implant of the present disclosure may be cut to fit a cartilage defect. The defect may be debrided and microfracture and/or microdrilling procedures may be performed at the site of the defect utilizing apparatus and methods within the purview of those skilled in the art. The implant of the present disclosure may be placed in the defect, with the PEG side down. Upon insertion into the defect, blood and fluids at the site of the defect wet the PEG, collagen, and salts. The first hydrogel precursor will be dissolved by the fluid. As the fluid wicks into and migrates across the implant, the fluid will carry the dissolved first hydrogel precursor along through the implant and into contact with the collagen and salts. The salts raise the pH, triggering a reaction between the electrophilic PEG and the collagen, resulting in gel formation within the cellulose and adhesion of the implant to the underlying subchondral bone and adjacent cartilage.

In addition to providing hemostasis and/or use for treating defects, for example cartilage defects, the implants may further be use for delivery of a bioactive agent. Thus, in some embodiments, at least one bioactive agent may be combined with either the first hydrogel precursor or the second hydrogel precursor and/or may be separately applied to the porous substrate. The agents may be freely admixed with the precursors or may be tethered to the precursors through any variety of chemical bonds. In these embodiments, the present implant can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present implant in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent in the bioactive coating of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in the coating composition applied in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g., lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

In some embodiments, liposomes containing bioactive agents, in embodiments growth factors, may be combined with a solution possessing at least one of the precursors, so that it becomes incorporated within the porous substrate. For example, in some cases, liposomes possessing at least one growth factor may be mixed with a buffer solution possessing nucleophilic precursors, such as collagen, and applied to the porous substrate, such as cellulose. In use, as a hydrogel forms upon the reaction of the collagen with the electrophilic PEG, the liposomes may be released. This may be useful, in embodiments, for cartilage repair, where the liposomes release growth factors at the site of a defect to stimulate regeneration of cartilage.

Figure 1B:
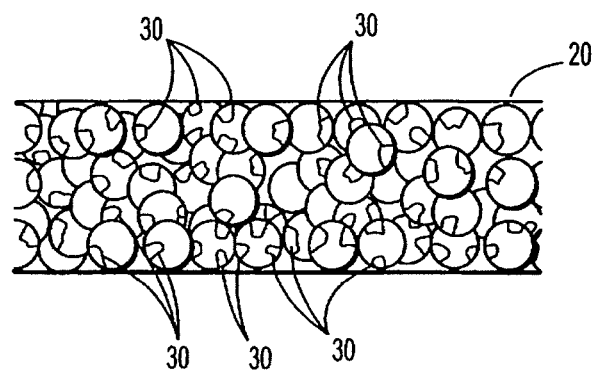

Turning now to FIGS. 1A-D, a sequence is shown wherein a first hydrogel precursor is applied within the pores of a porous substrate and a second hydrogel precursor is applied to a second portion of the porous substrate. In FIG. 1A, porous substrate 20 is a foam having a plurality of pores 25 defined therein. Solution 35, which includes a first hydrogel precursor dissolved in a solvent, is stored in container 19. Porous substrate 20 is dipped into and completely submerged within solution 35. Upon removal, the implant is dried, removing the solvent from solution 35 and depositing particles that include the first hydrogel precursor 30 within pores 25 of substrate 20, as shown in FIG. 1B.

Figure 1C:
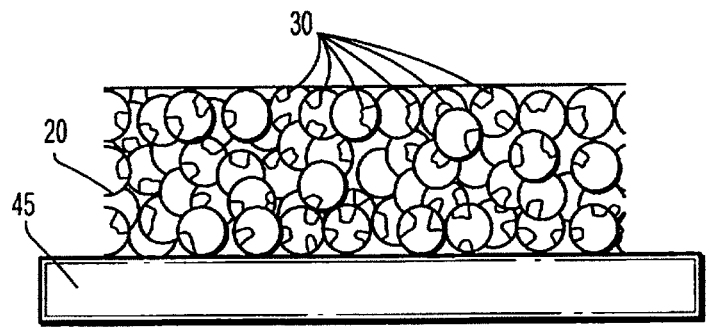
Figure 1D:
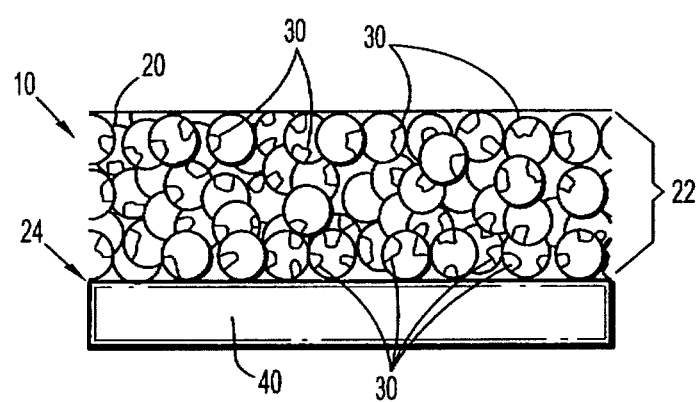

In FIG. 1C, porous substrate 20 containing the first hydrogel precursor is contacted with a melt 45 of the second hydrogel precursor. Upon cooling, the melt 45 of the second hydrogel precursor will solidify to form a film 40 over at least a portion of substrate 20. After application of the film 40 of the second precursor, the implant may be trimmed to any desired size and shape. Implant 10 of FIG. 1D is shown having a first hydrogel precursor in the form of particles 30 applied to a first portion 22 of the porous substrate 20 and a second hydrogel precursor in the form of a film 40 applied to a second portion 24 of the porous substrate 20.

Implant 110 of FIG. 2 is prepared in a manner similar to that show in the sequence of FIGS. 1A-D, with the exception that the porous substrate 120 is a mesh material having a first hydrogel precursor in the form of particles 130 and a second hydrogel precursor in the form of a film 140 applied thereto. It is contemplated that a non-woven material (not shown) may be used as the porous substrate instead of the foam shown in FIGS. 1A-D or the mesh shown in FIG. 2.

Figure 3:
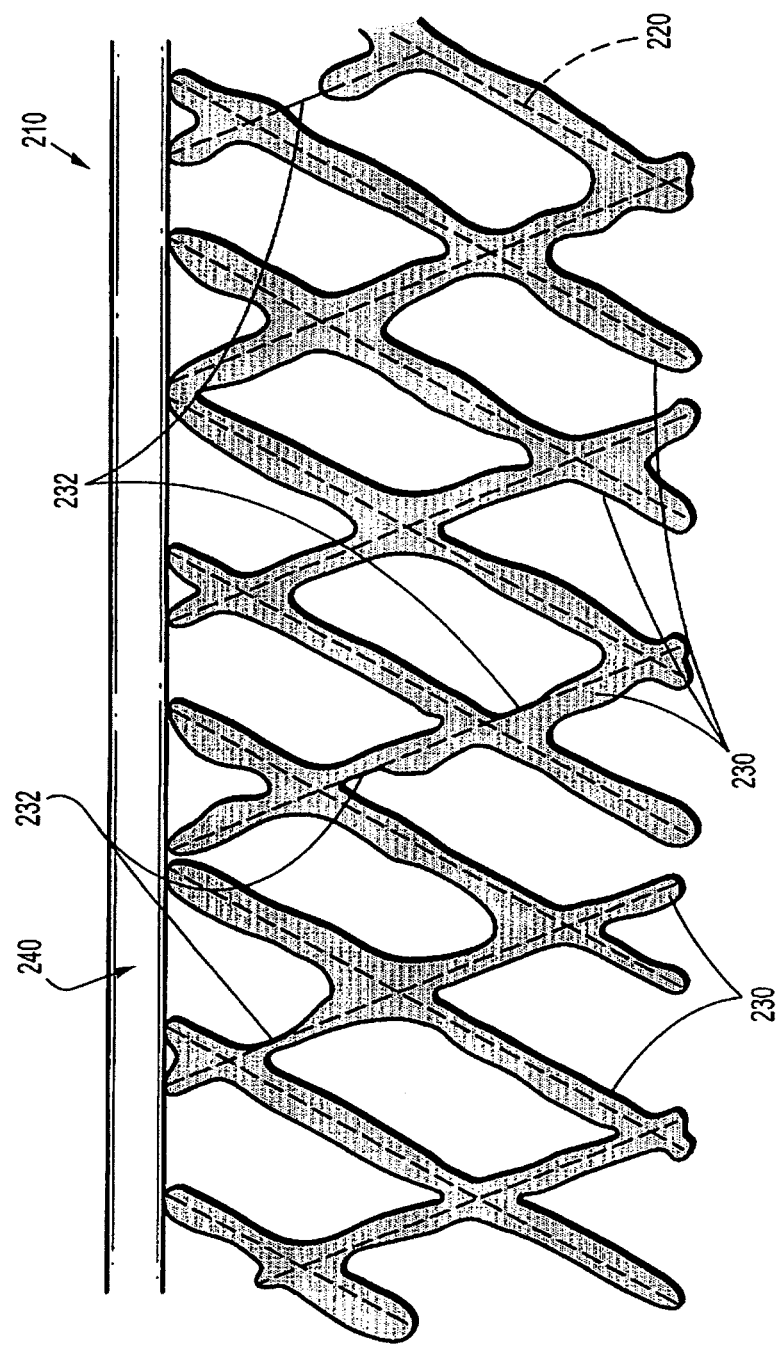
FIG. 3 schematically shows another variation of the embodiment shown in FIGS. 1A -1D.

Implant 210 of FIG. 3 is prepared in a manner similar to that shown in the sequence of FIGS. 1A-D, with the exception that the porous substrate 220 is a mesh material having a first hydrogel precursor in the form of a coating 230 and a second hydrogel precursor in the form of a film 240 applied thereto. Coating 230 of the first hydrogel precursor may be formed by immersing porous substrate 220 into a solution of the first hydrogel precursor or into a melt of the first hydrogel precursor. Alternatively, the first hydrogel precursor may be combined with a film-forming polymer prior to application to the substrate to provide coating 230. Those skilled in the art reading this disclosure will envision other method and materials for applying a coating containing the first hydrogel precursor to the substrate.

Figure 4A:
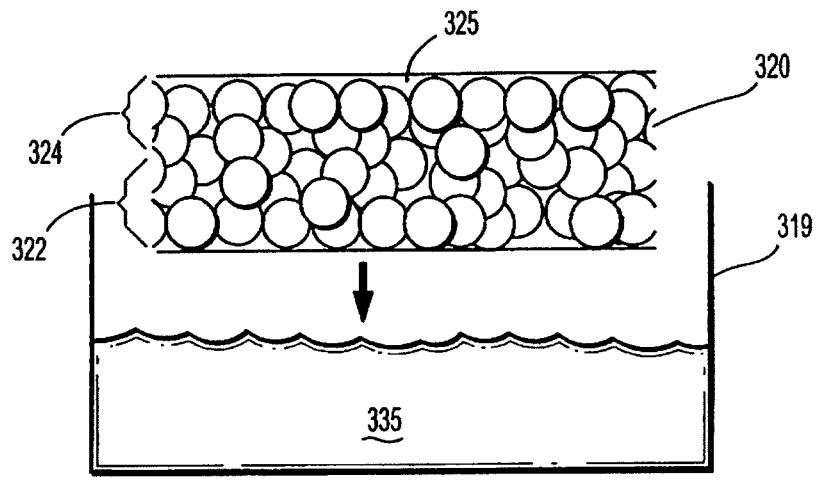
FIGS. 4A-C schematically show the application of a first hydrogel precursor to a porous substrate as described in at least one of the embodiments in the present disclosure.
Figure 4B:
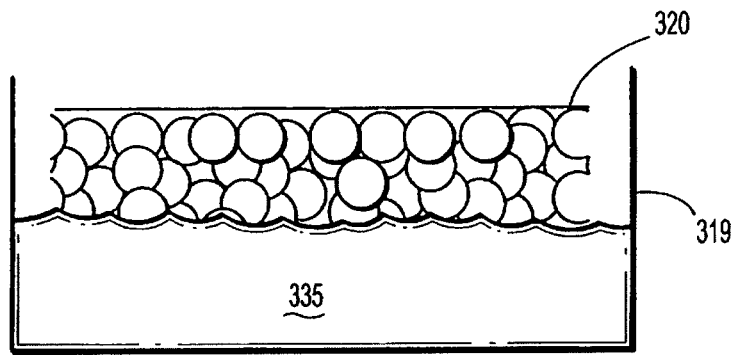
Figure 4C:
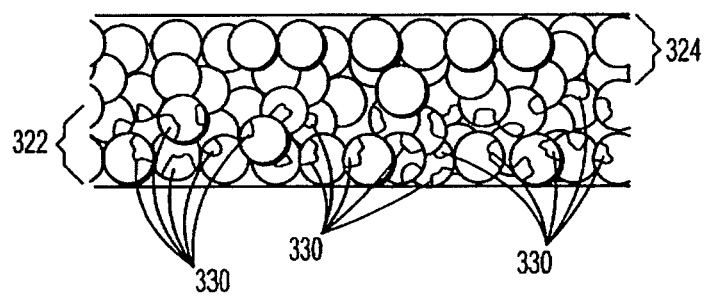

Turning now to FIGS. 4A-4C, a sequence is shown wherein a first hydrogel precursor is applied to a first portion of a porous substrate. In FIG. 4A, porous substrate 320 is a foam material having a plurality of pores 325 defined therein, which includes at least a first portion 322 and a second portion 324. Solution 335, which includes a first hydrogel precursor dissolved in a solvent, is stored in container 319. Porous substrate 320 is positioned over solution 335 with first portion 322 facing solution 335 and second portion 324 facing away from solution 335.

In FIG. 4B, first portion 322 of porous substrate 320 is partially submerged in solution 335 by moving porous substrate 320 in the direction of solution 335, as represented by the arrow in FIG. 4A. Only first portion 322 of porous substrate 320 comes in contact with solution 335 so that a sufficient amount of solution 335 may be applied to and fill the pores 325 of first portion 322 of porous substrate 320. Upon removal, the implant is dried, removing the solvent from solution 335 and depositing particles that include the first hydrogel precursor 330 in first portion 322, as shown in FIG. 4C. Particles 330 include the first hydrogel precursor in a dry format and are limited spatially to first portion 322.

Figure 5A:
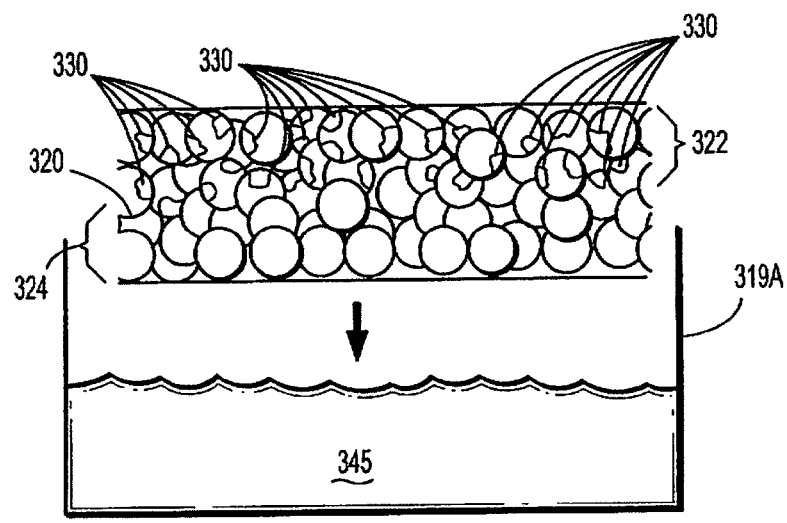
FIGS. 5A-C schematically show the application of particles including a second hydrogel precursor to a porous substrate already having a first hydrogel precursor applied thereto as described in at least one of the embodiments in the present disclosure.
Figure 5B:
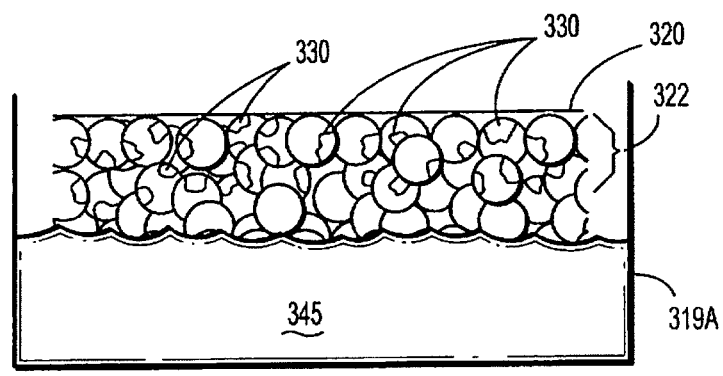
Figure 5C:
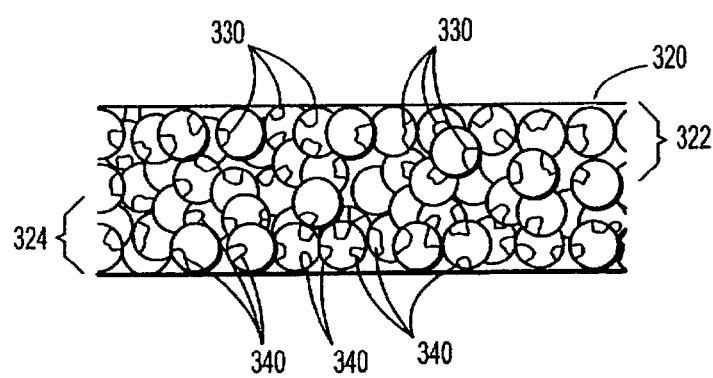

In FIGS. 5A-5C, a sequence is shown wherein solution 345 containing a second hydrogel precursor dissolved in a solvent is applied to second portion 324 of porous substrate 320, wherein particles 330 containing a first hydrogel precursor have been previously incorporated into first portion 322 of substrate 320 (See FIGS. 4A-4C). Porous substrate 320 is positioned over solution 345 with second portion 324 facing solution 345 and first portion 322 facing away from solution 345.

As shown in FIG. 5B, second portion 324 of porous substrate 320 is partially submerged in solution 345 by moving porous substrate 320 in the direction of solution 345, as represented by the arrow in FIG. 5A. Only second portion 324 of porous substrate 320 comes in contact with solution 345 so that a sufficient amount of solution 345 may be applied to second portion 324. Upon removal, the implant is dried to deposit second particles 340 including the second hydrogel precursor in second portion 324. Particles 340 include the second hydrogel precursor in a dry format and are limited spatially to second portion 324. Porous substrate 320 of FIG. 5C is shown having a first hydrogel precursor applied to a first portion of the substrate and a second hydrogel precursor applied to a second portion of the porous substrate with the first portion of the substrate being spatially separated from the second portion of the porous substrate.

In alternative embodiments, the first and second hydrogel precursors may be applied to the implant in different forms. For example, in FIGS. 6A-6C, porous substrate is shown including particles 430 including the first hydrogel precursor applied to first portion 422 with second portion 424 facing a film-forming solution 445 containing the second hydrogel precursor that has been applied to a support 429.

Figure 6A:
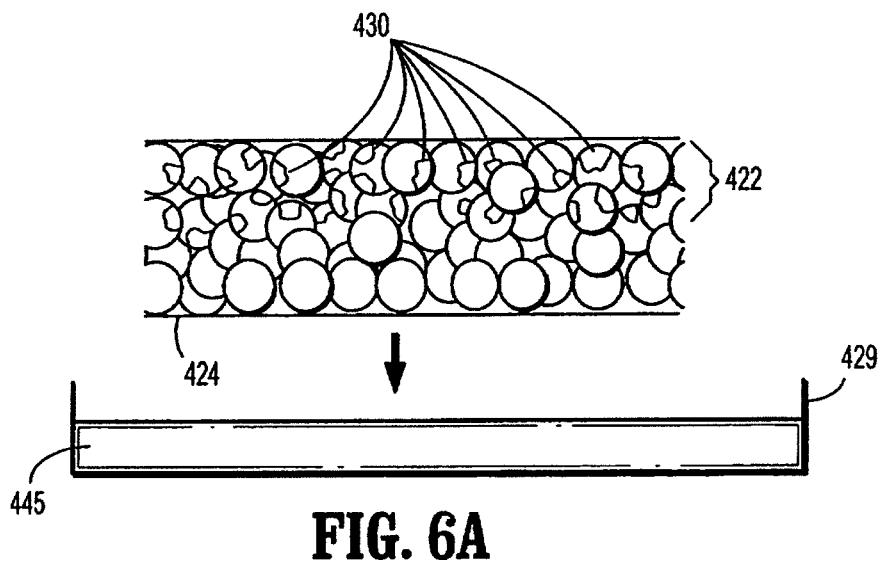
FIGS. 6A-C schematically show the application of a film containing a second hydrogel precursor to a porous substrate already having a first hydrogel precursor applied thereto as described in at least one of the embodiments in the present disclosure.
Figure 6B:
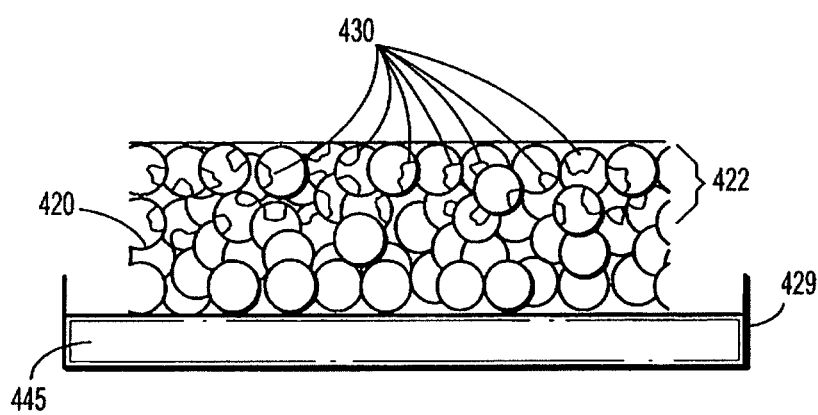
Figure 6C:
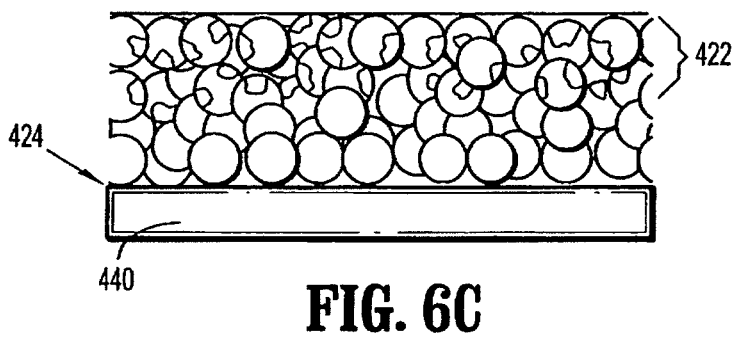

In FIG. 6B, second portion 424 of porous substrate 420 is contacted with and/or partially submerged in film-forming solution 445 by moving porous substrate 420 in the direction of shown by the arrow in FIG. 6A. Only second portion 424 of porous substrate 420 comes in contact with film-forming solution 445 so that a sufficient amount of material 445 may be applied to second portion 424. Film-forming solution 445 is allowed solidify (with or without the application of heat) to form a film 440 over at least a portion of second portion 424. Porous substrate 420 of FIG. 6C is shown having a first hydrogel precursor in the form of particles applied to a first portion of the substrate and a second hydrogel precursor in the form of a film 440 applied to a second portion of the porous substrate with the first portion of the substrate being spatially separated from the second portion of the porous substrate.

Figure 7A:
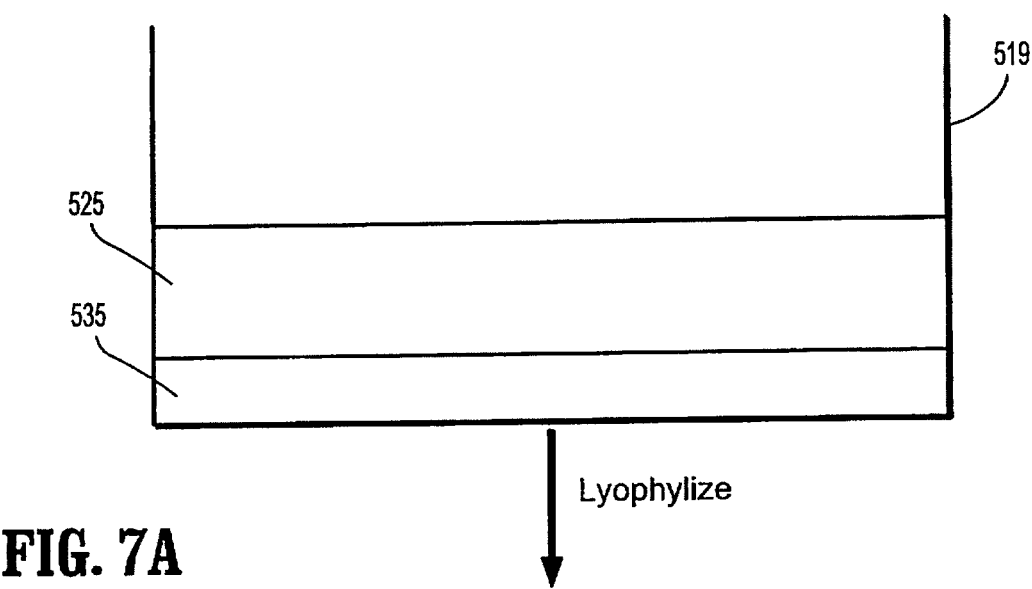
FIGS. 7A-B schematically show the simultaneous formation of a foam containing a first hydrogel precursor and a foam porous substrate.
Figure 7B:
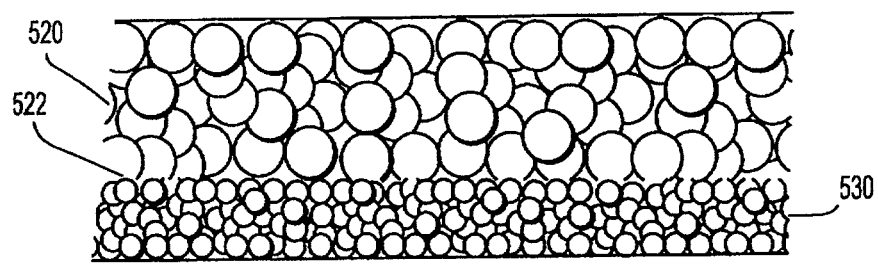

Turning now to FIGS. 7A-7B, the porous substrate and a porous layer including the first hydrogel precursor are shown formed together. In FIG. 7A, container 519 includes first solution 525 destined to form the porous substrate and a second solution 535 including the first hydrogel precursor, wherein the two solutions remain substantially as separate layers. The two solutions are lyophilized using any method known to those skilled in the art to form a porous substrate as shown in FIG. 7B, which includes first porous substrate 520, made from the lyophilized first solution 525, connected to a second porous layer 530, made from the lyophilized second solution 535. Second porous layer 530 contains the first hydrogel precursor and is bonded to first porous substrate 520 via first portion 522 to form an implant having two layers of porous material.

Figure 8A:
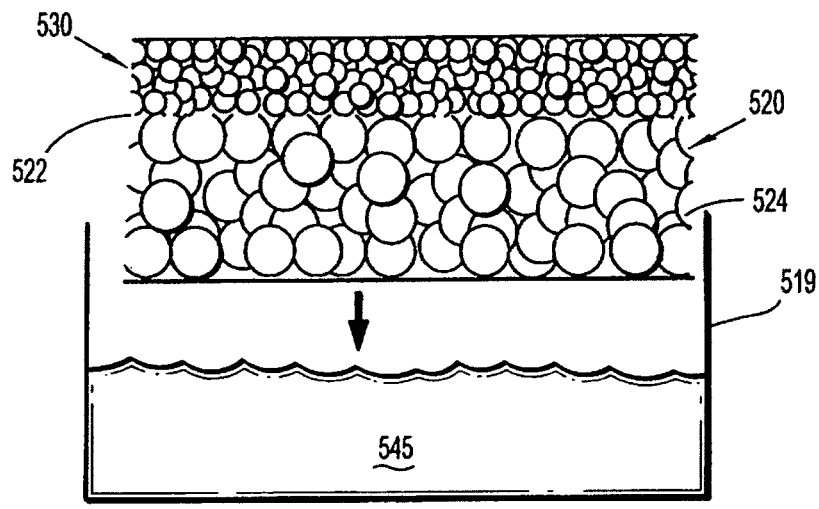
FIGS. 8A-C schematically show the application of particles including a second hydrogel precursor to a porous substrate already having a first hydrogel precursor applied thereto as described in at least one of the embodiments in the present disclosure.
Figure 8B:
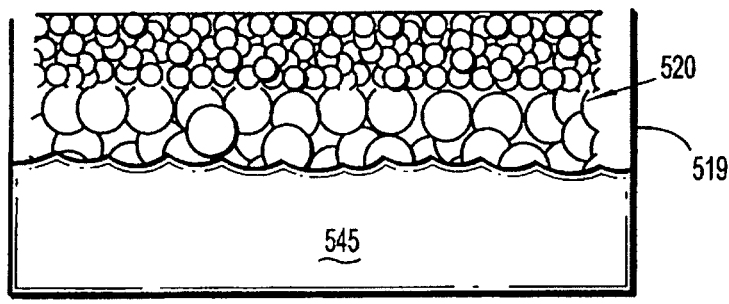
Figure 8C:
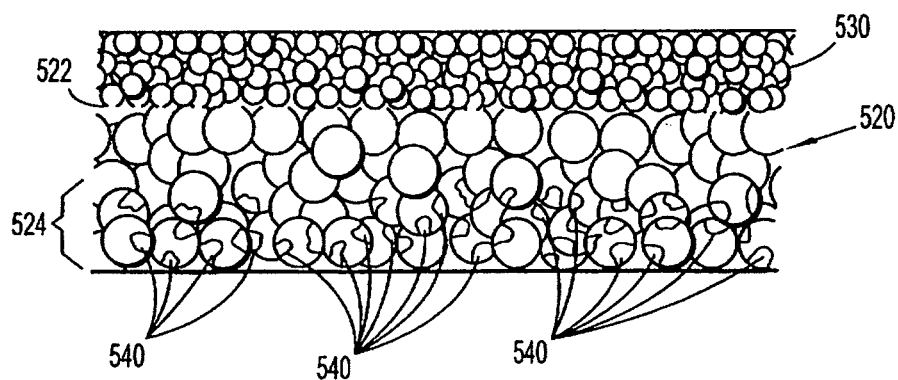

In FIGS. 8A-8C, a sequence is shown wherein solution 545 containing a second hydrogel precursor is applied to second portion 524 of porous substrate 520 already having substrate 530 including the first hydrogel precursor bonded thereto porous at first portion 522. Porous substrate 520 is positioned over solution 545 with second portion 524 facing solution 545 and first portion 522 and second porous layer 530 facing away from solution 545.

As shown in FIG. 8B, second portion 524 of porous substrate 520 is partially submerged in solution 545 having the first hydrogel precursor dissolved in a solvent by moving porous substrate 520 in the direction of solution 545, as represented by the arrow in FIG. 8A. Only second portion 524 of porous substrate 520 comes in contact with solution 545 so that a sufficient amount of solution 545 may be applied to second portion 524. Upon removal, the implant is dried or allowed to dry to remove the solvent and deposit particles 540 in second portion 524. Second particles 540 include the second hydrogel precursor in a dry format and are limited spatially to second portion 524. Porous substrate 520 of FIG. 8C is shown having a first hydrogel precursor in the form of a foam applied to a first portion of the substrate and a second hydrogel precursor in the form of particles applied to a second portion of the porous substrate with the first portion of the substrate being spatially separated from the second portion of the porous substrate.

Figure 9A:
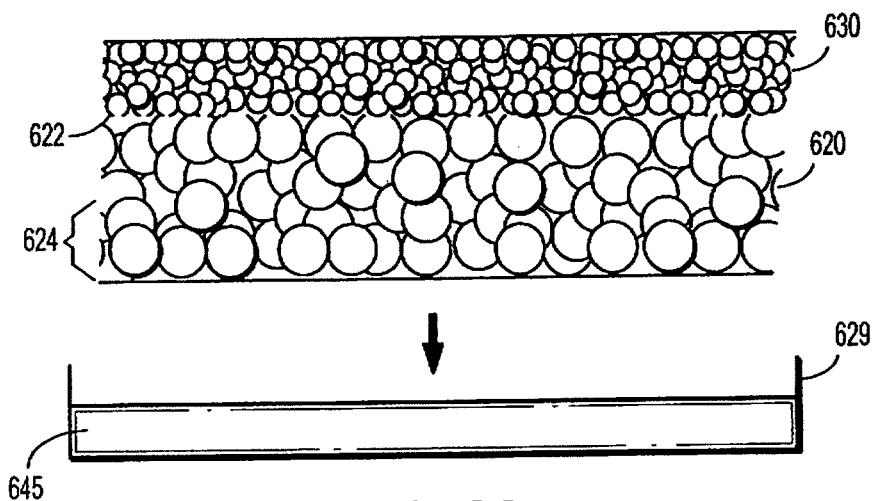
FIGS. 9A-C schematically show the application of a film containing a second hydrogel precursor to a porous substrate already having a first hydrogel precursor applied thereto as described in at least one of the embodiments in the present disclosure.
Figure 9B:
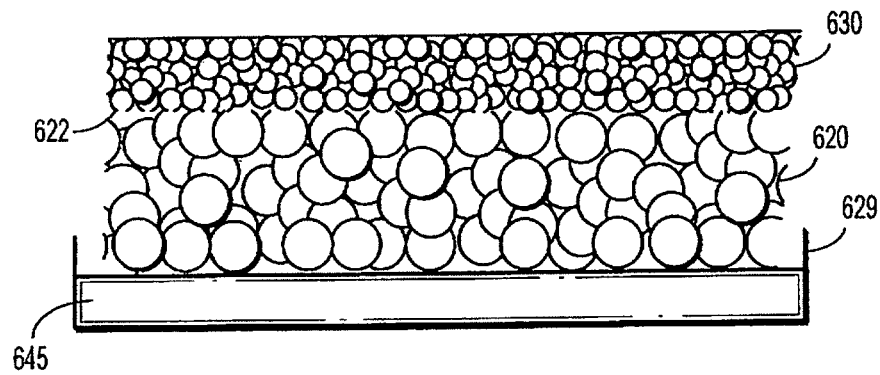
Figure 9C:
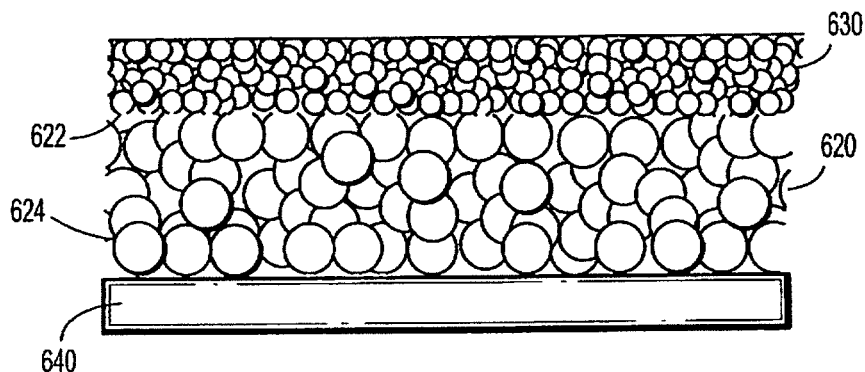

In an alternative embodiment, the porous substrate as shown in FIG. 7B may be combined with a film-forming material including the second hydrogel precursor. As shown in FIGS. 9A-9C, porous substrate 620 includes a first portion 622 and a second portion 624, wherein a second porous layer 630 containing a first hydrogel precursor is connected to porous substrate 620 at first portion 622. Second portion 624 is shown facing a film-forming solution 645 applied to support 629. Film-forming material 645 includes a second hydrogel precursor and a solvent.

In FIG. 9B, second portion 624 of porous substrate 620 is contacted with and/or partially submerged in film-forming solution 645 by moving porous substrate 620 in the direction of represented by the arrow in FIG. 9A. Only second portion 624 of porous substrate 620 comes in contact with film-forming solution 645 so that a sufficient amount of material 645 may be applied to second portion 624. Film-forming solution 645 is allowed to form a film 640 over at least a portion of second portion 624. Porous substrate 620 of FIG. 9C is shown having a first hydrogel precursor in the form of a foam applied to a first portion of the substrate and a second hydrogel precursor in the form of a film 640 applied to a second portion of the porous substrate with the first portion of the substrate being spatially separated from the second portion of the porous substrate.

Figure 10:
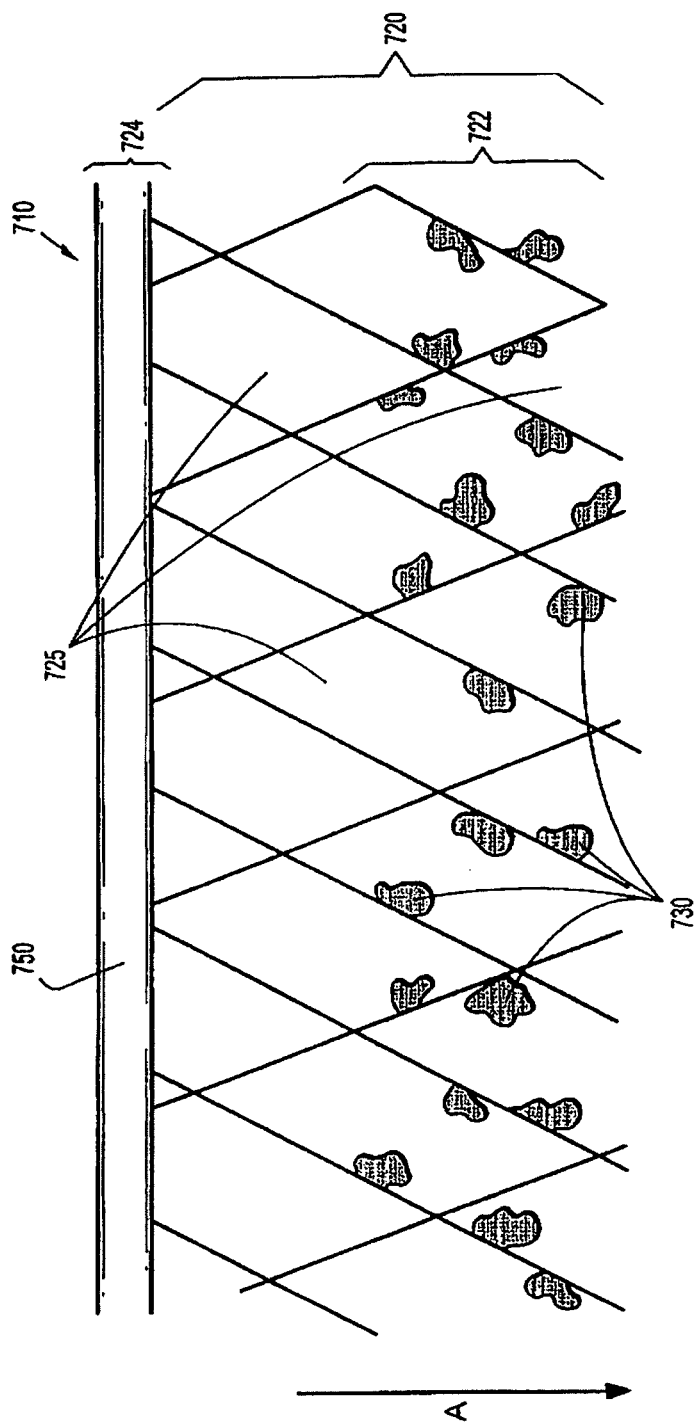
FIG. 10 schematically shows a knitted fibrous porous substrate having particles including a first hydrogel precursor applied to a first portion thereof and a film containing a second hydrogel precursor applied to second portion thereof as described in at least one of the embodiments in the present disclosure.

It should be understood that rather than a foam, as shown in FIGS. 4-9, the porous substrate may be a fibrous structure. Thus, in embodiments, and as shown schematically in FIGS. 10-12, the porous substrate may be a fibrous structure, i.e., a woven or non-woven structure. The first and second hydrogel precursors can be applied to a fibrous porous substrate using substantially the same techniques described above with respect to foam porous substrate 20. Accordingly, as with the foam porous substrates described above, where the porous substrate is fibrous, the first and/or second hydrogel precursors may be applied, for example as particles deposited from a solution, non-porous films formed by drying a film-forming solution, or as a foam applied to at least a portion of the fibrous porous substrate. As shown in FIG. 10, for example, implant 710 includes knitted porous substrate 720 including a plurality of pores 725 defined therein and having first portion 722 and second portion 724. Particles 730 containing a first hydrogel precursor in a dry format are applied to first portion 722 in a manner substantially similar to the manner shown above with respect to foam porous substrate 20, above in FIGS. 4A-C, for example. Film 750 containing a second hydrogel precursor is applied to second portion 724 in a manner substantially similar to the manner shown above with respect to foam porous substrate 320, above in FIGS. 5A-C, for example. Upon implantation, second portion 750 is applied to tissue in need of hemostasis. Upon contact with tissue, physiological fluids will penetrate implant 710 and migrate in the direction represented by arrow A thereby interacting with and liquefying film 750 before reaching particles 730. It is envisioned that as the fluids are wicked towards first portion 722 of substrate 720, a solution of film 750 will come in contact with particles 730 which will also be dissolved by and mix with the physiologic fluids. This mixing will activate the first and second precursors and allow them to interact and crosslink to form a seal assisting in the hemostatic function of the implant. In embodiments, this newly formed hydrogel/physiological fluid implant will also act as an adhesion barrier.

Figure 11:
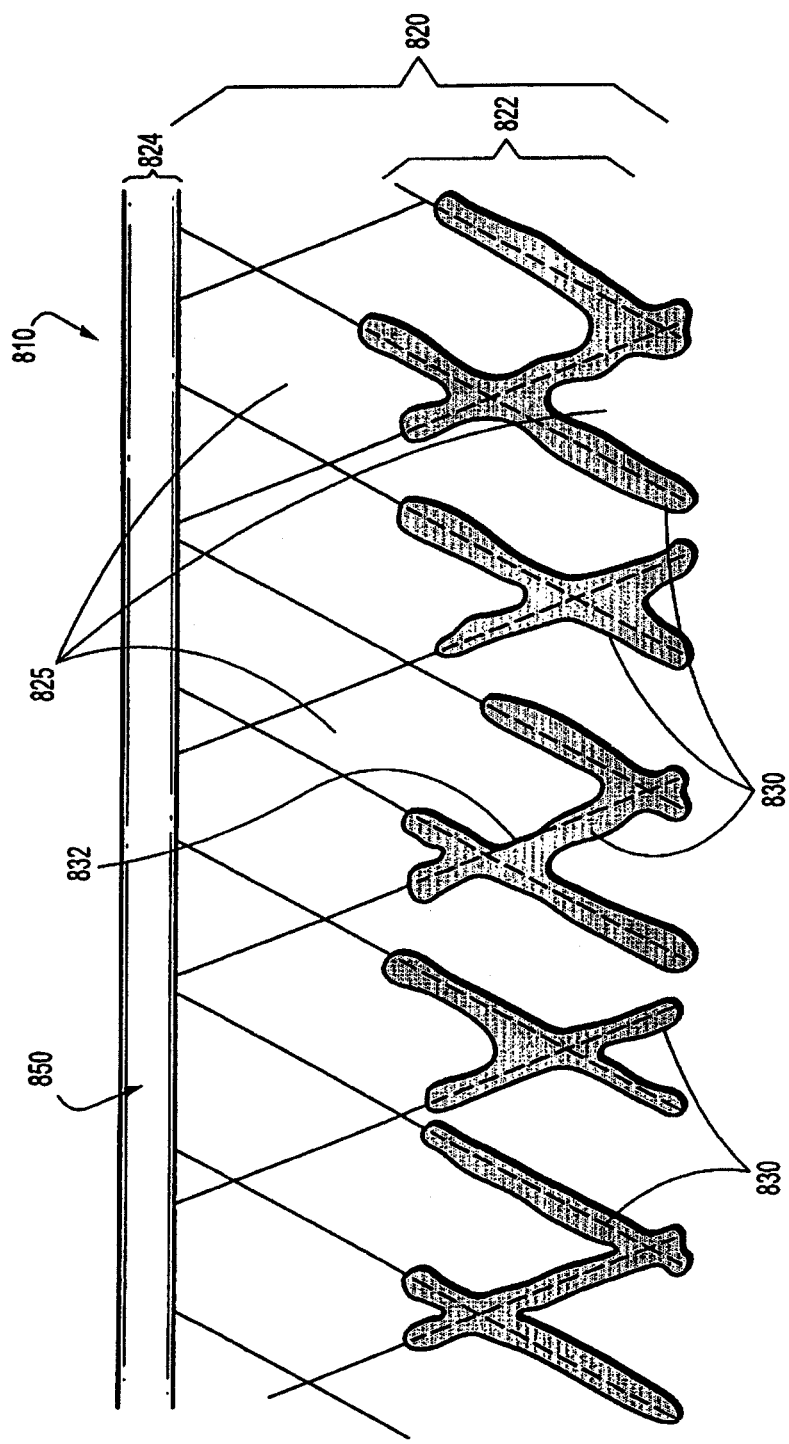
FIG. 11 schematically shows a knitted fibrous porous substrate having a coating including a first hydrogel precursor applied to a first portion thereof and a film containing a second hydrogel precursor applied to second portion thereof as described in at least one of the embodiments in the present disclosure.

It is further contemplated that the first and/or second hydrogel precursor may be applied from a melt containing the first and/or second hydrogel precursor rather than from a solution. In FIG. 11, for example, implant 810 includes a knitted porous substrate 820 having first portion 822 and second portion 824 wherein second portion 824 again includes film 850 which contains a second hydrogel precursor. In this embodiment, however, the first hydrogel precursor 830 is applied as a coating to first portion 822 from a melt rather than as particles from a solution. As shown, melt 830 essentially coats at least a portion of the fibers of first portion 822 of substrate 820 while allowing pores 825 to remain sufficiently open to allow the migration of fluids through porous substrate 820. It should be understood that the coating 830 may be discontinuous, leaving portions 832 of the substrate 820 may uncoated.

Figure 12:
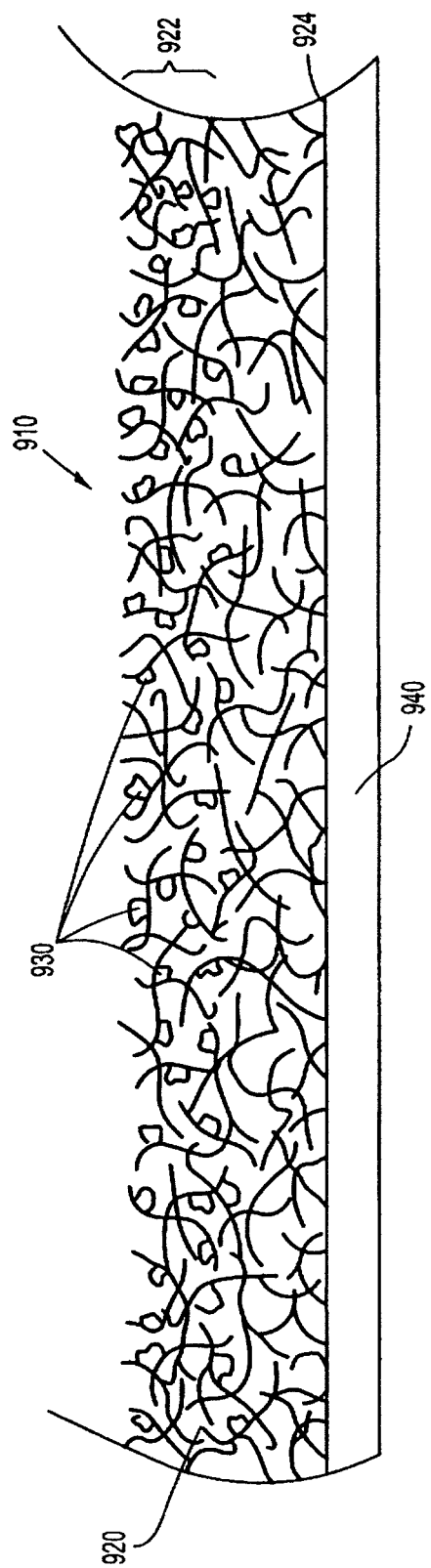
FIG. 12 schematically shows a non-woven fibrous porous substrate having particles including a first hydrogel precursor applied to a first portion thereof and a film containing a second hydrogel precursor applied to second portion thereof as described in at least one of the embodiments in the present disclosure.

As noted above, the porous substrate may be a non-woven fibrous porous substrate. In FIG. 12, for example, implant 910 is shown as a non-woven porous substrate 920 having a first portion 922 and second portion 924 wherein particles 930 including the first hydrogel precursor applied to first portion 922 and a film 940 including the second hydrogel precursor applied to second portion 924.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature from about 20° C. to about 25° C.

EXAMPLES

Example 1

A saturated borate buffer solution of trilysine is prepared. The solution contains 20.6 milligrams of trilysine per milliliter of solution. The pH of the solution is about 9.2. A sheet of oxidized cellulose is dipped into the solution and then fixed to a rack for drying. The rack is placed into a vacuum oven. The oven is pumped down to about 50 mTorr and kept at a temperature of about 25° C. for about three days to reduce the moisture level to less than 2% by weight. An eight arm N-hydroxysuccinimidyl-functionalized polyethylene glycol having a molecular weight of about fifteen thousand is melted at about 50° C. on a hot plate. The dried trilysine-containing oxidized cellulose sheet is placed into contact with the melted PEG component. After cooling, the PEG component forms a film on one side of the implant.

The resulting product is trimmed to a 2 inch by 2 inch square, dried and packaged in a foil container.

In use, the foil package is opened and the implant is applied to a bleeding wound with the PEG film side against the wound. Within seconds, hemostasis occurs.

Example 2

A saturated borate buffer solution of collagen is prepared. The solution contains 10-60 milligrams of collagen per milliliter of solution. The pH of the solution is about 9.2. A sheet of oxidized cellulose is dipped into the solution and then fixed to a rack for drying. The rack is placed into a vacuum oven. The oven is pumped down to about 50 mTorr and kept at a temperature of about 25° C. for about three days to reduce the moisture level to less than 2% by weight. An eight arm N-hydroxysuccinimidyl-functionalized polyethylene glycol having a molecular weight of about fifteen thousand is melted at about 50° C. on a hot plate. The dried collagen-containing oxidized cellulose sheet is placed into contact with the melted PEG component. After cooling, the PEG component forms a film on one side of the implant.

The resulting product is trimmed to a 2 inch by 2 inch square, dried and packaged in a foil container.

In use, the foil package is opened and the implant is applied to a cartilage defect with the PEG film side down. Upon insertion into the defect, blood and fluids at the site of the defect wet the PEG, collagen, and salts. The PEG film is dissolved by the fluids at the site of the defect. As the fluids wick into and migrate across the implant, the fluids will carry the dissolved PEG along through the implant and into contact with the collagen and salts. The salts will raise the pH, triggering a reaction between the electrophilic PEG and the collagen, and will form a gel within the cellulose so that adhesion of the implant to the underlying subchondral bone and adjacent cartilage will occur.

It will be understood that various modifications may be made to the embodiments disclosed herein. For example, more than two precursors may be applied to the porous substrate to form the hemostatic implant. As another example, the first and second precursors may each be applied to the porous substrate as a film. Thus, those skilled in the art will envision other modifications within the scope and spirit of the claims.

What is claimed is:

1. An implant comprising:
   a porous substrate having a first hydrogel precursor comprising collagen applied to the porous substrate; and
   a film containing a second hydrogel precursor formed of a water soluble polymer including polyethylene glycol, polyethylene oxide, polyethylene oxide-co-polypropylene oxide, co-polyethylene oxide block or random copolymers, polyvinyl alcohol, poly(vinyl pyrrolidinone), dextran, chitosan, alignates, carboxymethycellulose, oxidized cellulose, hydroxyethylcellulose, hyaluronic acid, or combinations thereof, the water soluble polymer functionalized to possess electrophilic groups, the film applied to the porous substrate,
   wherein the first hydrogel precursor is spatially separated from the second hydrogel precursor, and the first hydrogel precursor is configured to react with the second hydrogel precursor upon contact with bodily fluid after implantation, thereby forming a hydrogel.

2. The implant of claim 1, wherein the porous substrate is a foam.

3. The implant of claim 1, wherein the porous substrate is a knitted textile.

4. The implant of claim 1, wherein the porous substrate is a non-woven textile.

5. The implant of claim 1, wherein the porous substrate is made from a bioabsorbable material.

6. The implant of claim 1, wherein the porous substrate is made from a non-bioabsorbable material.

7. The implant of claim 1, wherein the porous substrate is made from oxidized cellulose.

8. The implant of claim 1, wherein the first hydrogel precursor comprises particles.

9. The implant of claim 1, wherein the first hydrogel precursor further comprises at least one basic salt comprising borates, carbonates, phosphates, bicarbonates, and combinations thereof.

10. The implant of claim 1, further comprising a bioactive agent.

11. An implant comprising:
    a porous substrate having a first hydrogel precursor comprising collagen applied to a first portion of the porous substrate; and
    a second hydrogel precursor formed of a water soluble polymer including polyethylene gylcol, polyethylene oxide, polyethylene oxide co-polypropylene oxide, co-polyethylene oxide block or random copolymers, polyvinyl alcohol, poly(vinyl pyrrolidinone), dextran, chitosan, alginates, carboxymethylcellulose, oxidized cellulose, hydroxyethylcellulose, hyaluronic acid, or combinations thereof, the water soluble polymer functionalized to possess electrophilic groups, the second hydrogel precursor applied to a second portion of the porous substrate,
    wherein the first portion of the porous substrate is spatially separated from the second portion of the porous substrate, the first hydrogel precursor is spatially separated from the second hydrogel precursor, and the first hydrogel precursor is configured to react with the second hydrogel precursor upon contact with bodily fluid after implantation, thereby forming a hydrogel.

12. The implant of claim 11, wherein the porous substrate is a foam.

13. The implant of claim 11, wherein the porous substrate is a knitted textile.

14. The implant of claim 11, wherein the porous substrate is a non-woven textile.

15. The implant of claim 11, wherein the porous substrate is made from a bioabsorbable material.

16. The implant of claim 11, wherein the porous substrate is made from a non-bioaborbable material.

17. The implant of claim 11, wherein the porous substrate is made from oxidized cellulose.

18. The implant of claim 11, wherein the first hydrogel precursor comprises particles.

19. The implant of claim 11, wherein the second hydrogel precursor is a foam.

20. The implant of claim 11, wherein the second hydrogel precursor is a film.

21. The implant of claim 11, further comprising a bioactive agent.

22. The implant of claim 11, wherein the first hydrogel precursor further comprises at least one basic salt comprising borates, carbonates, phosphates, bicarbonates, and combinations thereof.

23. The implant of claim 1, wherein the second hydrogel precursor comprises a polyethylene glycol functionalized with N-hydroxysuccinimides.

24. The implant of claim 11, wherein the second hydrogel precursor comprises a polyethylene glycol functionalized with N-hydroxysuccinimides.

* * * * *